United States Patent [19]

Weiss

[11] Patent Number: 5,167,074
[45] Date of Patent: Dec. 1, 1992

[54] APPARATUS FOR POSITIONING A MULTIFOCAL SEGMENT ON AN EYEGLASS LENS AND METHOD OF USE

[76] Inventor: Michael E. Weiss, 8609 - 50th Ave. North, New Hope, Minn. 55428

[21] Appl. No.: 577,854

[22] Filed: Sep. 5, 1990

[51] Int. Cl.⁵ .............................................. A61B 3/10
[52] U.S. Cl. ..................................... 33/200; 251/204
[58] Field of Search ............... 351/204; 33/200, 507, 33/511, 512; 128/645, 647, 648, 650, 651, 652

[56] References Cited

U.S. PATENT DOCUMENTS

| | | | |
|---|---|---|---|
| 2,011,308 | 8/1935 | Williams | 33/200 |
| 2,024,194 | 12/1935 | Wyckoff. | |
| 2,043,230 | 6/1936 | Boll et al. | 33/200 X |
| 3,706,304 | 12/1972 | Sisler. | |
| 4,055,900 | 11/1977 | Grolman et al. | |
| 4,494,837 | 1/1985 | Bommarito. | |
| 4,653,192 | 3/1987 | Conrad et al. | 33/200 |
| 4,653,881 | 3/1987 | Joncour | 33/200 X |

*Primary Examiner*—Harry N. Haroian
*Attorney, Agent, or Firm*—Moore & Hansen

[57] ABSTRACT

A device for measuring the dimensions for locating multifocal segments on eyeglass lenses. A chinrest is provided for maintaining the stability of the patient's head while the proper location of the multifocal segment is determined, and an eyepiece is provided through which the dispenser may look at reference points on the face of the patient and the patient's new eyewear to measure the required dimensions. The eyepiece is then moved along the vertical axis of the post to which it is mounted, and the distance traveled by the eyepiece between the reference points is measured by a measuring device found on the apparatus.

6 Claims, 1 Drawing Sheet

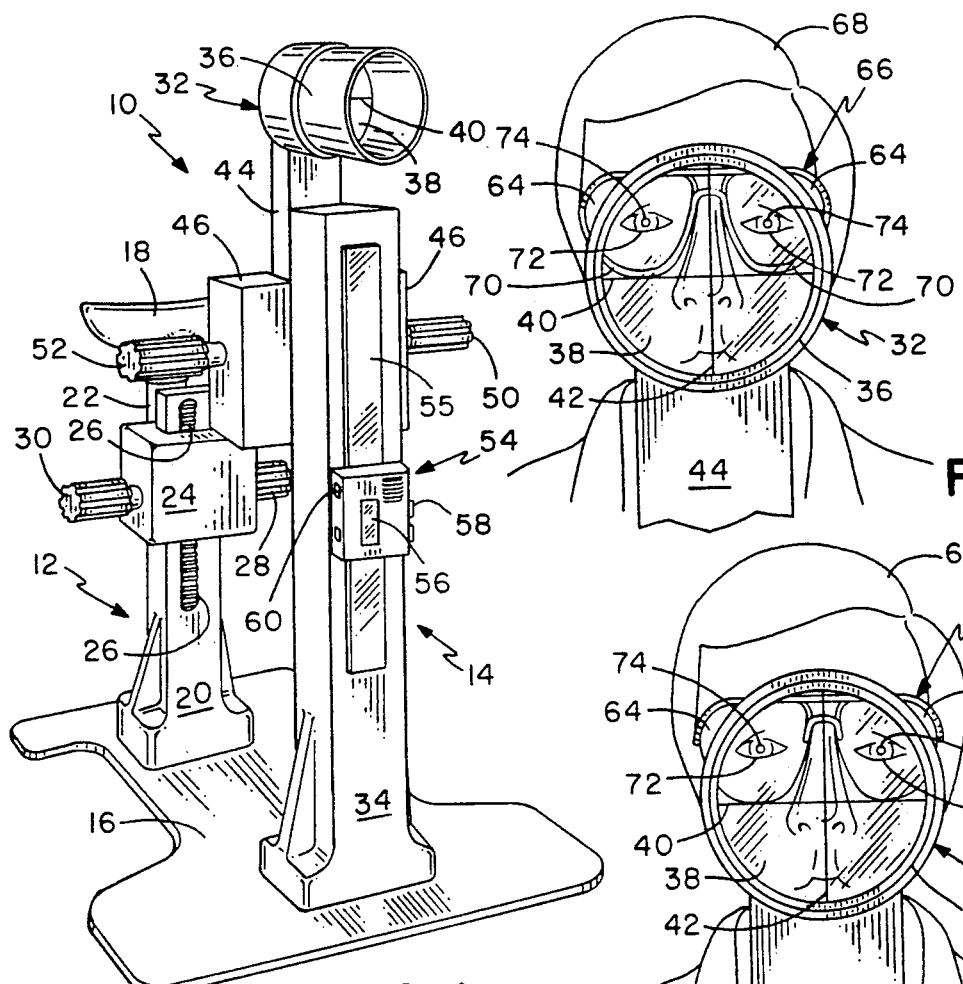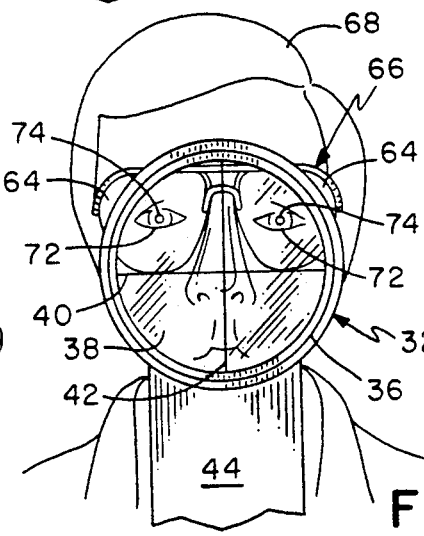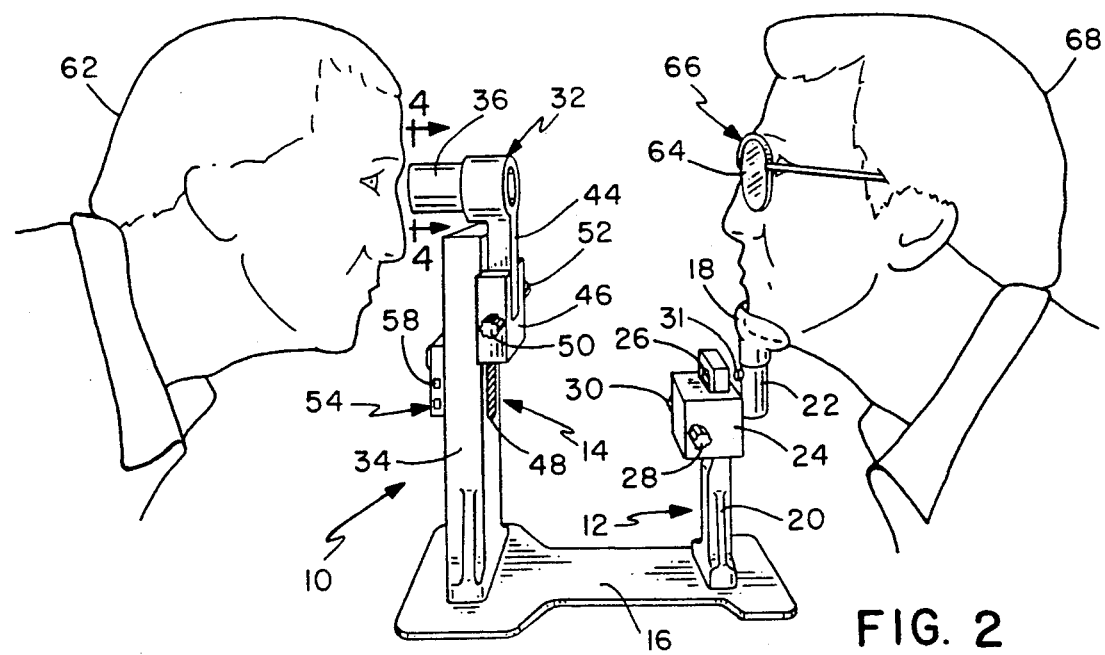

APPARATUS FOR POSITIONING A MULTIFOCAL SEGMENT ON AN EYEGLASS LENS AND METHOD OF USE

BACKGROUND OF THE INVENTION

1. Technical Field

The present invention relates generally to devices used for positioning b ocal and trifocal segments on the lenses of corrective eyewear, and more particularly to such devices that rest on a table top and on which the person being fitted for new glasses rests their chin, yet are lightweight and easily moved from one location to another.

2. Background Information

A very large segment of the population wears corrective eyewear to aid a variety of vision problems. Many of these people need assistance with focusing on both distant and close objects For those people, corrective eyewear having bifocal lenses and sometimes trifocal lenses may be necessary. The specially ground portion of the lens containing the bifocal or bifocal and trifocal segment, which is intended more particularly to help in viewing nearby objects, is known generally as the multifocal segment. In order for the multifocal segment to provide the greatest assistance to the person wearing the eyewear, while minimizing the amount of interference with distant viewing, the multifocal segment must be precisely positioned on the lens.

Certain instruments and techniques have been developed and incorporated into what have become known as "conventional methods" for properly positioning the multifocal segment on an eyeglass lens. Among these methods is the use of a millimeter ruler held in the hand of the dispenser, the person who fits the eyewear on the patient, the person who is being fitted for eyewear. Using this method, as with any method of positioning the multifocal segment on the eyeglass lenses, it is important that the dispenser have available the frames that the patient has selected, and that the frames already be properly fitted to the patient. The dispenser places the frames on the patient, and then measures the distance from the bottom of the lens for rimless frames, or the bottom of the frame eyewire, to the location on the patient with which the upper edge of the multifocal segment should be aligned. For visible bifocal lenses, the dispenser measures to where the eyelashes grow from underneath the patient's eye. For no-line bifocal lenses, the dispenser measures to the center of the patient's pupil. For trifocal lenses, the dispenser measures to just below the pupil. This measurement is recorded for each eye, and the distance measured determines the position on the lens for locating the upper edge of the multifocal segment.

There are several potential sources for inaccuracy in this method. It is very important when using this method to align properly the millimeter ruler to make accurate measurements, and many dispensers become quite proficient at this. However, there are many circumstances when even the most able dispensers have difficulty keeping their measurements accurate. For example, an elderly patient may become fatigued from maintaining their head in an upright position while the dispenser makes the appropriate measurements. Likewise, a patient with Parkinson's disease may not be able to maintain a steady head position with any amount of effort. The dispenser may also become while trying to make an accurate measurement and trying to adopt to the peculiar problems a patient may have with holding their head steady. If there is a height disparity between the patient and the dispenser, the measurements also may be adversely affected by the dispenser's attempt to look directly at the face of the patient, if in fact the dispenser does not adequately compensate for the height difference. Some patients are not comfortable with having a ruler held close to their face, right in front of their eyes, and may flinch, shake or otherwise make the measurements very difficult to take with accuracy. Measurement taken in this way may also be time-consuming since it is frequently necessary to double-check dimensions if the patient's head is moving.

Other devices have been developed for measuring these distances. U.S. Pat. No. 4,055,900 for a DEVICE FOR MAKING OPTHALMIC [sic] MEASUREMENTS AND METHOD, issued to Grolman et al. on Nov. 1, 1977, discloses a device fitted to the frames selected by the patient, the whole assembly then being fitted to the face of the patient. The device, while capable of making relatively accurate measurements, is heavy, and may slide down the nose of the patient, distorting the measurements taken by the dispenser. Similarly, U.S. Pat. No. 4,653,192 for a SEGMENT HEIGHT MEASURING DEVICE, issued to Conrad et al. on Mar. 31, 1987, and U.S. Pat. No. 4,494,837 for a PUPIL LOCATION GAUGE, issued to Bommarito on Jan. 22, 1985, also disclose a device that is fitted to the frames selected by the patient Although lighter in weight than the device of Grolman et al., these devices also require the dispenser to be positioned directly perpendicular to the eyes of the patient to take an accurate measurement. However, if the device is too heavy or uncomfortable for the patient, especially an elderly patient or one suffering from Parkinson's, as described-above, it may be difficult if not impossible to maintain the patient's head in the proper position for accurately determining the needed dimensions.

SUMMARY OF THE INVENTION

The invention includes a base portion having two upright portions extending therefrom. The first upright portion contains a chinrest, and the second upright portion contains an eyepiece and a means for measuring the displacement of the eyepiece in the vertical plane. The eyepiece contains a lens that has a horizontal crosshair and preferably a vertical crosshair. After placing a pair of properly fitted frames of the patient's choosing on the patient, the dispenser positions the patient's chin on the chinrest, making it easier for patients to keep their heads in proper position. The dispenser may then observe the patient through the eyepiece and make the appropriate measurements by repositioning the eyepiece in the vertical plane. A vernier with a digital readout measures the distance traveled by the eyepiece, and thus determine the required dimensions.

It is an object of the invention to provide a device and method for using the device that reduces the likelihood of error in measuring the dimensions needed for proper placement of the multifocal segment on the lenses of corrective eyewear.

It is a further object of the invention to provide the dispenser with a device that is faster and more accurate to use when recording the measurements needed for positioning the multifocal segment on eyeglass lenses.

It is a further object of the invention to provide a device that is easy enough to use that an inexperienced dispenser or technician could use it and take measurements with the same level of accuracy as an experienced dispenser.

Other objects and advantages of the invention will become apparent from the following detailed description and from the appended drawings in which like numbers have been used to describe like parts throughout the several views.

BRIEF DESCRIPTION OF THE DRAWINGS

FIG. 1 shows a perspective view of an apparatus for positioning a multifocal segment on an eyeglass lens constructed according to the invention;

FIG. 2 shows a side view of the apparatus in use by a dispenser and a patient;

FIG. 3 shows the dispenser's view through the eyepiece of the invention of a patient wearing eyeglasses having eyewires surrounding the lenses; and FIG. 4 shows the dispenser's view through the eyepiece of the invention of a patient wearing rimless eyeglasses.

DESCRIPTION OF THE PREFERRED EMBODIMENT

With reference to the drawings, and in particular to FIG. 1, the apparatus for positioning a multifocal segment on an eyeglass lens is generally indicated by reference numeral 10. Upright chin support assembly 12 and upright eyepiece support assembly 14 project from base portion positioning apparatus 10.

As is most clearly shown in FIGS. 1 and 2, upright chin support assembly 12 includes a chinrest 18 mounted on the upper end of chin support post 20. While chinrest 18 may be mounted to chin support post 20 in a fixed position, it is preferred that chinrest 18 be adjustable along the vertical axis of chin support post 20. Thus, chinrest 18 is attached to chinrest mount 22 projecting from chinrest adjusting bracket 24. Chinrest adjusting bracket 24 contains gears (not shown) that mesh with serrated segment 26 of chin support post 20, as shown in FIG. 1. Chinrest adjustment knob 28 may be rotated as necessary to locate chinrest 18 in a desired position, and chinrest locking knob 30 may then be rotated to lock chinrest adjusting bracket 24 and chinrest 18 in the desired position. Chinrest 18 is preferably made of plastic, and may easily be replaced within chinrest mount 22 as necessary by loosening set screw 31 before removing an old chinrest 18, and then retightening set screw 31 after inserting a new chinrest 18.

Upright eyepiece support assembly 14 includes an eyepiece 32 mounted on the upper end of eyepiece support post 34. As shown in FIGS. 3 and 4, eyepiece 32 includes a cylindrical viewer 36 having at least one non-magnifying lens 38 mounted therein. Lens 38 includes a horizontal crosshair 40 and preferably also includes a vertical crosshair 42. Eyepiece 32 is attached to eyepiece mount 44, which in turn is fastened to eyepiece adjusting bracket 46. Eyepiece adjusting bracket 46 contains gears (not shown) that mesh with serrated segment 48 of eyepiece support post 34, as shown in FIG. 2. Eyepiece adjustment knob 50 may be rotated as necessary to locate eyepiece 32 in a desired position, and eyepiece locking knob 52 may then be rotated to lock eyepiece adjusting bracket 46 in the desired position, although eyepiece locking knob 52 is not normally utilized except when the apparatus is temporarily out of use.

In its preferred embodiment, the major structural components of the apparatus for positioning a multifocal segment 10, including base portion 16, chin support post 20, and eyepiece support post 4, are made of aluminum, although the gears in chinrest adjusting bracket 24 and eyepiece adjusting bracket 46 may be made of plastic. It is preferred that device 10 weigh between 6½ and 7½ pounds, with a preferred weight of approximately seven pounds. Base portion 16 is preferably approximately twelve inches long, chin support post 20 is preferably approximately 7¼ inches tall, and eyepiece support post 34 is preferably approximately eleven inches tall. Adjustments to chinrest adjustment knob 28 permit chinrest 18 to be adjusted between heights of approximately eleven inches and 9½ inches above the surface on which device 10 is resting. Similarly, adjustments to eyepiece adjustment knob 50 permit horizontal crosshair 40 of eyepiece 32 to be adjusted between heights of approximately 12¼ inches and 14½ inches above the surface on which device 10 is resting Eyepiece 32 is approximately three inches long and 1½ inches in diameter, and the distance between the patient's end of eyepiece 32 and the front of patient's eyeglass lens 64 is between approximately 6¾ inches and seven inches.

Upon adjusting eyepiece 32 along the vertical axis of eyepiece support post 34, the distance traveled may be determined using a glass slide vernier 54 that travels along glass scale 55, although it is known that a number of other measuring devices (e.q., sliding analog rulers or circular gauges) are available for determining these measurements. Vernier 54 is attached to eyepiece adjusting bracket 46 through grooved openings (not shown) in eyepiece support post 34, and interacts with glass scale 55 to determine a distance traveled. It is preferred that vernier 54 or other measuring device record the distance traveled by the eyepiece in millimeters. It is also preferred that vernier 54 includes a quartz digital readout 56 of the measurement taken by vernier 54. The preferred vernier is a battery operated model manufactured by MITUTOYO. To make a measurement, a zero button 58 on vernier 54 is pressed, setting digital readout 56 to zero. Upon rotating eyepiece adjustment knob 50 to reposition eyepiece 32, the reading on digital readout 56 changes to reflect the distance traveled by eyepiece 32 in millimeters. Once a reading has been taken, lock button 60 may be pressed to maintain the same reading on digital readout 56 regardless of whether eyepiece adjustment knob 50 is rotated to reposition eyepiece 32.

In use, a dispenser 62 locates the dimensions of a multifocal segment or segments on the lenses 64 of a new set of corrective eyewear 66 of a patient 68. The corrective eyewear 66 may be rimless as shown in FIG. 4 or it may have eyewires 70 around lenses 64 as shown in FIG. 3. Before dispenser 62 measures for the location of the multifocal segment on lenses 64, patient 68 will have already selected new eyewear 66, and the eyewear will have been properly fitted to the particular patient. Dispenser 62 will then place eyewear 66 on the patient 68, making sure it is comfortably positioned as it would be during normal use. Patient 68 will then place their chin on chinrest 18, and dispenser 62 will rotate chinrest adjustment knob 28 until chinrest 1B is at a comfortable height for patient 68, and then lock chinrest 18 in that position using chinrest locking knob 30. It is important that chinrest 18 be locked in its proper position since, if the patient 68 leans too heavily on chinrest 18 without it being locked in position, chinrest adjusting bracket 24 may move downward somewhat along the vertical axis of chin support post 20, possibly causing the measurements taken by dispenser 62 to be erroneous.

Once patient 68 is properly positioned, dispenser 62 looks through viewer 36 of eyepiece 32 at patient 68. Patient 68 should be positioned in such a manner that vertical crosshair 42 is aligned along the middle of the patient's nose. If patient 68 has eyewires 70 around lenses 64 as shown in FIG. 3, dispenser 62 aligns horizontal crosshair 40 with the bottom edge of eyewire 70 by rotating eyepiece adjustment knob 50. If patient 68 has rimless eyewear as in FIG. 2, dispenser 62 aligns horizontal crosshair 40 with the bottom edge of lenses 64 by rotating eyepiece adjustment knob 50. Once horizontal crosshair 40 is properly aligned, dispenser 62 presses zero button 58 on vernier 54 to set digital readout 56 to zero. Dispenser 62 then looks above the top of eyepiece 32 directly at patient 68 at the physical feature of patient 68 which serves as a reference point with which dispenser 62 will next align horizontal crosshair 40, and then turns eyepiece adjustment knob 50 to adjust eyepiece 32 upwardly until horizontal crosshair 40 is aligned with that reference point. For visible bifocal lenses, dispenser 62 aligns horizontal crosshair 40 with the place 72 where the eyelashes grow from underneath the patient's eye. For no-line bifocal lenses, dispenser 62 aligns horizontal crosshair 40 with the center of pupil 74 of patient 68. For trifocal lenses, dispenser 62 aligns horizontal crosshair 40 with a location just below the pupil 74 of patient 68. After aligning horizontal crosshair 40 with the desired reference point of paitnt 68, dispenser 62 looks at digital readout 56 of vernier 54 and records on the patient's paperwork the measurement displayed there. Optionally, dispenser 62 may record the measurement on a printer connected to vernier 54 should such an option be desired. These steps have been described under the assumption that the multifocal segments of both lenses 64 are to be positioned simultaneously. However, the same steps would also be followed for an individual eye if the multifocal segment needed to be positioned on each eye separately or if the multifocal segment was to be positioned on one eye only.

While the preferred embodiments of the invention have been described, it should be understood that various changes, adaptations, and modifications may be made therein without departing from the spirit of the invention and the scope of the appended claims.

What is claimed is:

1. A method for using an apparatus for positioning at least one multifocal segment on at least one eyeglass lens to be inserted in the lens area of a set of properly fitted eyeglass frames for eyeglasses to be worn by a person, comprising the steps of:
   plaing the frames in which the lens will be installed on the person;
   positioning the chin of the person on a chinrest integral with said apparatus;
   looking through an eyepiece integral with said apparatus at the person;
   locating said eyepiece to a first position by aligning a horizontal crosshair in a lens in said eyepiece with a reference point on the eyeglasses, said eyeglass reference point being near the bottom of the lens;
   relocating said eyepiece to a second position by re-aligning said horizontal crosshair in said lens of said eyepiece with a facial reference point on the person; and
   measuring the distance traveled by said eyepiece between said first position and said second position.

2. A method for using a multifocal segment locating apparatus as recited in claim 1, further comprising:
   repositioning said chinrest to a height most comfortable for the person after positioning the chin of the person on said chinrest integral with said apparatus.

3. The method for using a multifocal segment locating apparatus as recited in claim 1, further comprising:
   looking at the person above said eyepiece after locating said eyepiece to said first position; and
   focusing on the facial reference point on the person while relocating said eyepiece to said second position.

4. A method for using a multifocal segment locating apparatus as recited in claim 1, wherein:
   said step of measuring the distance traveled by said eyepiece is carried out with a vernier.

5. A method for using a multifocal segment locating apparatus as recited in claim 4, further comprising:
   zeroing said vernier after locating said eyepiece to said first position.

6. A method for using a multifocal segment locating apparatus as recited in claim 5, further comprising:
   looking at the person above said eyepiece after zeroing said vernier; and
   focusing on the facial reference point on the person while relocating said eyepiece to said second position.

* * * * *

UNITED STATES PATENT AND TRADEMARK OFFICE
CERTIFICATE OF CORRECTION

PATENT NO. : 5,167,074
DATED : December 1, 1992
INVENTOR(S) : Weiss, Michael E.

It is certified that error appears in the above-indentified patent and that said Letters Patent is hereby corrected as shown below:

```
Col. 1, line 9, delete "bocal" and substitute —bifocal—.
        line 19, after "objects" insert —.—.
Col. 2, line 30, after "patient" insert —.—.
Col. 4, line 4, delete "4" and substitute —34—.
        line 15, delete "eleven" and substitute -7-1/4—.
        line 63, delete "1B" and substitute —18—.
Col. 5, line 32, delete "paitnt" and substitute —patient—.
```

Signed and Sealed this

Fourth Day of January, 1994

Attest:

BRUCE LEHMAN

*Attesting Officer*     *Commissioner of Patents and Trademarks*